US012171452B2

(12) United States Patent
Brause

(10) Patent No.: US 12,171,452 B2
(45) Date of Patent: Dec. 24, 2024

(54) DRIVE ROD AND KNIFE BLADE FOR AN ARTICULATING SURGICAL INSTRUMENT

(71) Applicant: Covidien LP, Mansfield, MA (US)

(72) Inventor: David D. Brause, Longmont, CO (US)

(73) Assignee: Covidien LP, Mansfield, MA (US)

( * ) Notice: Subject to any disclaimer, the term of this patent is extended or adjusted under 35 U.S.C. 154(b) by 100 days.

(21) Appl. No.: 17/981,693

(22) Filed: Nov. 7, 2022

(65) Prior Publication Data
US 2023/0053807 A1 Feb. 23, 2023

Related U.S. Application Data

(62) Division of application No. 16/832,886, filed on Mar. 27, 2020, now Pat. No. 11,490,917.
(Continued)

(51) Int. Cl.
*A61B 17/295* (2006.01)
*A61B 17/3211* (2006.01)
(Continued)

(52) U.S. Cl.
CPC ........ *A61B 17/295* (2013.01); *A61B 17/3211* (2013.01); *A61B 2017/00734* (2013.01);
(Continued)

(58) Field of Classification Search
CPC .............. A61B 17/295; A61B 17/3211; A61B 17/320092; A61B 18/085; A61B 18/1445;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Julian W Woo

(57) ABSTRACT

A surgical instrument includes a housing including an actuator disposed thereon and an elongated shaft extending therefrom. The elongated shaft includes an end effector assembly including a pair of opposing jaw members including a knife channel defined therein. An articulation section is disposed between the housing and the end effector assembly and is configured to articulate the end effector assembly upon actuation of the actuator, the articulating section and a proximal end of the knife channel defining a first distance therebetween. A knife assembly includes a knife having a length, the proximal end including an engagement feature disposed thereon. A knife drive rod is configured to engage the engagement feature to secure the knife drive rod to the knife such that the distal end of the knife extends beyond the engagement feature and wherein the knife length is less than the length of the first distance.

17 Claims, 7 Drawing Sheets

Related U.S. Application Data

(60) Provisional application No. 62/825,870, filed on Mar. 29, 2019.

(51) Int. Cl.

| | | |
|---|---|---|
| A61B 17/00 | (2006.01) | |
| A61B 17/32 | (2006.01) | |
| A61B 18/00 | (2006.01) | |
| A61B 18/08 | (2006.01) | |
| A61B 18/14 | (2006.01) | |
| A61B 18/18 | (2006.01) | |
| A61B 34/35 | (2016.01) | |

(52) U.S. Cl.
CPC ........... *A61B 2017/00867* (2013.01); *A61B 17/320092* (2013.01); *A61B 2018/00077* (2013.01); *A61B 2018/00589* (2013.01); *A61B 2018/00595* (2013.01); *A61B 2018/0063* (2013.01); *A61B 18/085* (2013.01); *A61B 18/1445* (2013.01); *A61B 2018/1455* (2013.01); *A61B 2018/1807* (2013.01); *A61B 2018/1823* (2013.01); *A61B 34/35* (2016.02)

(58) Field of Classification Search
CPC .... A61B 18/00589; A61B 2018/00595; A61B 2018/1455
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 10,888,322 B2 * | 1/2021 | Morgan .................. A61B 34/30 |
| 11,717,294 B2 * | 8/2023 | Huitema .......... A61B 17/07207 227/176.1 |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |

FOREIGN PATENT DOCUMENTS

| | | | |
|---|---|---|---|
| DE | 02514501 A1 | 10/1976 | |
| DE | 2627679 A1 | 1/1977 | |
| DE | 03423356 C2 | 6/1986 | |
| DE | 03612646 A1 | 4/1987 | |
| DE | 3627221 A1 | 2/1988 | |
| DE | 8712328 U1 | 3/1988 | |
| DE | 04303882 C2 | 2/1995 | |
| DE | 4403252 A1 | 8/1995 | |
| DE | 19515914 C1 | 7/1996 | |
| DE | 19506363 A1 | 8/1996 | |
| DE | 29616210 U1 | 11/1996 | |
| DE | 19608716 C1 | 4/1997 | |
| DE | 19751106 A1 | 5/1998 | |
| DE | 19751108 A1 | 5/1999 | |
| DE | 19946527 C1 | 7/2001 | |
| DE | 20121161 U1 | 4/2002 | |
| DE | 10045375 C2 | 10/2002 | |
| DE | 202007009165 U1 | 8/2007 | |
| DE | 202007009317 U1 | 8/2007 | |
| DE | 202007009318 U1 | 8/2007 | |

(56) References Cited

FOREIGN PATENT DOCUMENTS

| | | |
|---|---|---|
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 1192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.

Peterson et al. "Comparison of Healing Process Following Ligation with Sutures and Bipolar Vessel Sealing" Surgical Technology International (2001).

Electrosurgery: A Historical Overview Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al., "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room"; Sales/Product Literature, Valleylab 2001.

Bergdahl et al. "Studies on Coagulation and the Development of an Automatic Computerized Bipolar Coagulator" J. Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. Jul. 1, 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C .. (1 Page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Heniford et al. "Initial Research and Clinical Results with an Electrothermal Bipolar Vessel Sealer" Oct. 1999. (1 page).

\* cited by examiner

DRIVE ROD AND KNIFE BLADE FOR AN ARTICULATING SURGICAL INSTRUMENT

CROSS REFERENCE TO RELATED APPLICATIONS

This application is a divisional of U.S. patent application Ser. No. 16/832,886 filed Mar. 27, 2020, which claims the benefit of and priority to U.S. Provisional Patent Application No. 62/825,870, filed on Mar. 29, 2019, the entire contents of all of the foregoing applications are incorporated by reference herein.

BACKGROUND

Technical Field

The present disclosure relates surgical instruments, and more particularly, to a drive rod and knife blade for use with an articulating surgical forceps.

Background of Related Art

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife or cutting member utilized to effectively sever the treated tissue.

Many electrosurgical forceps include various actuators to orient the jaw members for tissue treatment. For example, many forceps include rotational wheels (or the like) disposed in proximity to a surgeon's hands to enable the surgeon to selectively rotate the jaw members as needed during an operation. A trigger (or similar) may be disposed on the forceps housing to allow a surgeon to selectively deploy a knife or cutting element as needed during surgery. Other actuators include articulating mechanisms disposed in proximity to the surgeon's hands to allow the surgeon to selectively articulate (e.g., pitch and yaw) the jaw members as needed during surgery.

With particular respect to articulating forceps that include a deployable knife, one important feature of these types of forceps is the knife drive rod which typically needs to be both sufficiently flexible to allow articulation of the jaw members while also being strong enough to advance and retract a knife blade through tissue. Another design consideration with articulating forceps is to minimize the distance from the articulation region to the jaw members commonly referred to as "dead space". By minimizing this distance, usability and surgical access is improved. In other words and as mentioned above because of the articulating joints, a flexible wire or tube is typically used to advance and retract the knife blade. The length of the knife blade attached to the flexible wire is a constraint for dead space, e.g., the knife should not retract behind the tissue stop of the jaw members (little or no portion of the knife blade should retract into any of the articulation joints (unless specifically designed for a particular purpose). However, this constraint typically dictates that additional length must be added to the forceps to house the retracted knife blade between the jaw member and articulating joint, i.e., a longer knife blade naturally means a longer distance between the jaw members and the articulation joint and undesirable dead space.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

In accordance with aspects of the present disclosure, a surgical instrument includes a housing having one or more actuators disposed thereon and an elongated shaft extending from a distal portion of the housing. The elongated shaft includes an end effector assembly engaged at a distal end thereof having a pair of opposing jaw members, at least one of the jaw members including a knife channel defined therein. An articulation section is disposed between the housing and the end effector assembly and is configured to selectively articulate the end effector assembly upon actuation of the actuator(s). The articulating section and a proximal end of the knife channel define a first distance therebetween. A knife assembly includes a knife having proximal and distal ends defining a knife length therebetween, the proximal end including an engagement feature disposed thereon. A knife drive rod is configured to operably engage the engagement feature to secure the knife drive rod to the knife such that the distal end of the knife extends beyond the engagement feature and wherein the knife length is less than the length of the first distance.

In aspects according to the present disclosure, the engagement feature of the knife assembly includes one or more capture tabs disposed within in an aperture defined within the proximal end of the knife. In other aspects according to the present disclosure, the knife assembly includes: a tube configured to operably engage the capture tab(s) disposed within the aperture; and a knife drive rod configured to operably engage the tube disposed within the aperture.

In aspects according to the present disclosure, a weld operably engages the tube to the knife. In yet other aspects according to the present disclosure, the knife and the tube are made from similar metals to increase the strength of the weld. In still other aspects according to the present disclosure, the distal end of the knife drive rod threadably engages the tube.

In yet other aspects according to the present disclosure, the engagement feature includes an aperture defined within the knife, the aperture configured to receive a bent end of the knife drive rod. In still other aspects according to the present disclosure, the engagement feature of the knife includes an aperture defined in the proximal end of the knife that includes a series of spaced apart fins extending thereacross and the knife drive rod is configured to operably engage the fins to secure the knife drive rod to the knife. In aspects according to the present disclosure, the knife drive rod is configured to engage the fins in a weave-like manner from a proximal end of the aperture to a distal end of the aperture. In still other aspects according to the present disclosure, a retention mechanism is operably disposed at a distal end of the knife drive rod and is configured to secure the knife drive rod in engagement between the fins.

In aspects according to the present disclosure, the engagement feature includes one or more detents disposed on a proximal end of the knife and the knife drive rod includes one or more complementary apertures defined therein configured to engage the one or more detents to secure the knife to the knife drive rod. In other aspects according to the present disclosure, the one or more detents is welded within the aperture.

In accordance with aspects of the present disclosure, a surgical instrument includes a housing having one or more actuators disposed thereon and an elongated shaft extending from a distal portion of the housing. The elongated shaft includes an end effector assembly engaged at a distal end thereof that includes a pair of opposing jaw members, at least one of the jaw members including a knife channel defined therein. An articulation section is disposed between the housing and the end effector assembly and is configured to selectively articulate the end effector assembly upon actuation of the actuator(s). The articulating section and a proximal end of the knife channel define a first distance therebetween. A knife assembly includes: a knife having proximal and distal ends that define a knife length therebetween that is less than the length of the first distance; and a knife drive rod welded to the knife.

In aspects according to the present disclosure, the weld formed between the knife and the knife drive rod is disposed on a proximal end of the knife. In other aspects according to the present disclosure, the weld formed between the knife and the knife drive rod is disposed along an inner surface of the knife.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1A:
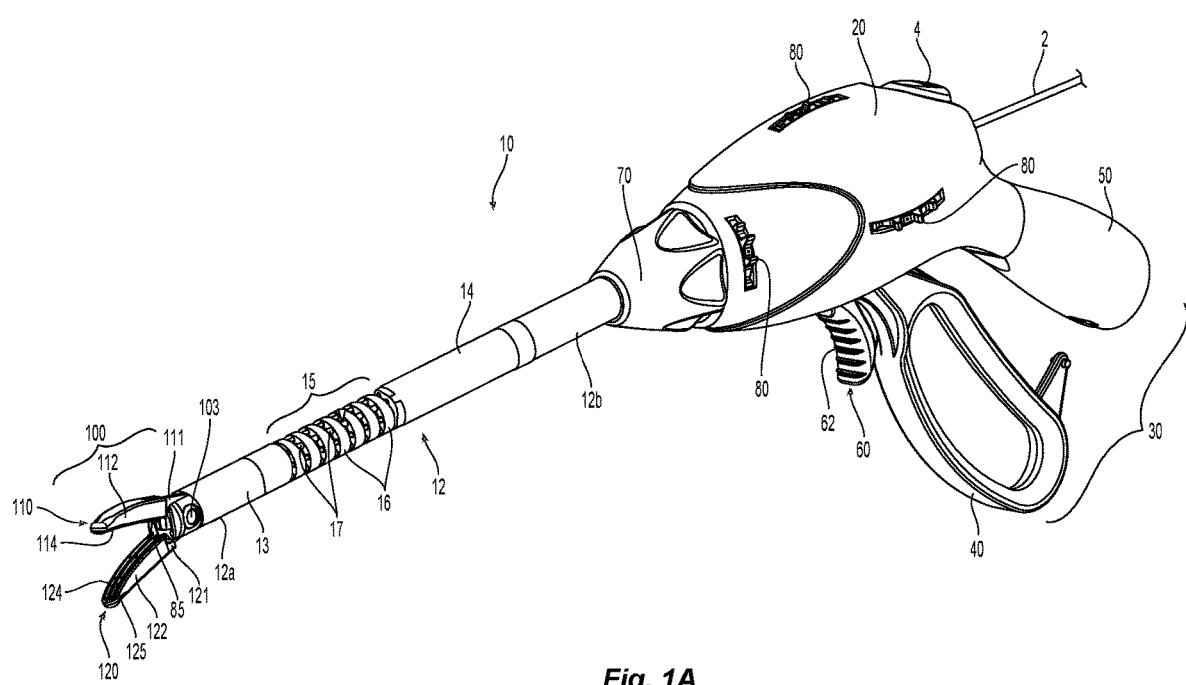
FIG. 1A is a perspective view of endoscopic surgical forceps exemplifying the aspects and features of the present disclosure, wherein the shaft of the endoscopic surgical forceps is disposed in a non-articulated position and wherein the jaw members of the endoscopic surgical forceps are disposed in a spaced-apart position.
Figure 1B:
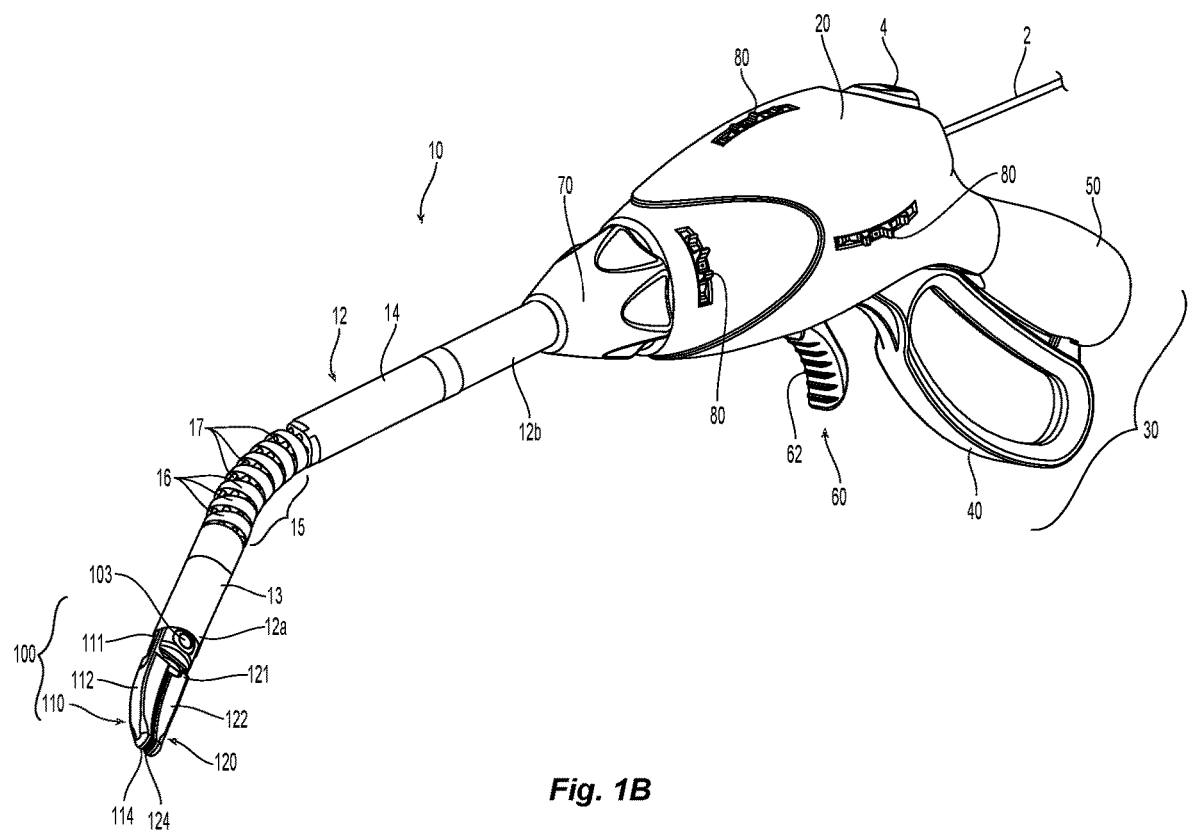
FIG. 1B is a perspective view of the endoscopic surgical forceps of FIG. 1A, wherein the shaft of the endoscopic surgical forceps is disposed in an articulated position and wherein the jaw members of the endoscopic surgical forceps are disposed in an approximated position.

Referring generally to FIGS. 1A and 1B, an endoscopic surgical forceps exemplifying the aspects and features of the present disclosure is shown generally identified by reference numeral 10. For the purposes herein, endoscopic surgical forceps 10 is generally described. Aspects and features of endoscopic surgical forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, a plurality of articulation actuators 80, an activation switch 4, and an end effector assembly 100. Forceps 10 further includes a shaft 12 having a distal end 12a configured to mechanically engage end effector assembly 100 and a proximal end 12b that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating plates 114, 124 of jaw members 110, 120, respectively, of end effector assembly 100. Activation switch 4 is coupled to tissue-treating plates 114, 124 and the source of energy for selectively activating the supply of energy to jaw members 110, 120 for treating, e.g., cauterizing, coagulating/desiccating, and/or sealing, tissue.

Shaft 12 of forceps 10 defines a distal segment 13 positioned towards distal end 12a thereof, a proximal segment 14 positioned towards proximal end 12b thereof, and an articulating section 15 disposed between the distal and proximal segments 13, 14, respectively. Articulating section 15 includes a plurality of articulating links 16 having a plurality of articulation cables 17 extending therethrough. Each cable 17 is operably engaged at a distal end thereof to distal segment 13 and at a proximal end thereof to one of the articulation actuators 80 to enable articulation of distal segment 13 and, thus, end effector assembly 100, relative to proximal segment 14 upon actuation of one or more of articulation actuators 80. Rotating assembly 70 operably couples shaft 12 to housing 20 to enable selective rotation of shaft 12 and, thus, end effector assembly 100, relative to housing 20.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position (FIG. 1A) and an approximated position (FIG. 1B) to grasp tissue between jaw members 110, 120. As shown in FIG. 1A, movable handle 40 is initially spaced-apart from fixed handle 50 and, correspondingly, jaw members 110, 120 of end effector assembly 100 are disposed in the spaced-apart position. Movable handle 40 is compressible from this initial position to a compressed position corresponding to the approximated position of jaw members 110, 120 (FIG. 1B).

Trigger assembly 60 includes a trigger 62 coupled to housing 20 and movable relative thereto between an un-actuated position and an actuated position. Trigger 62 is operably coupled to a cutting mechanism 85, various embodiments of which are detailed below, to actuate the cutting mechanism 85 to cut tissue grasped between jaw members 110, 120 of end effector assembly 100 upon actuation of trigger 62. As an alternative to a pivoting trigger 62, a slide trigger, push-button, toggle switch, or other suitable actuator may be provided.

End effector assembly 100, as noted above, includes first and second jaw members 110, 120. Each jaw member 110, 120 includes a proximal flange portion 111, 121, an outer insulative jaw housing 112, 122 disposed about the distal portion (not explicitly shown) of each jaw member 110, 120, and a tissue-treating plate 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw members 110, 120 are configured to support jaw housings 112, 122, and tissue-treating plates 114, 124, respectively, thereon.

Outer insulative jaw housings 112, 122 of jaw members 110, 120 support and retain tissue-treating plates 114, 124 on respective jaw members 110, 120 in opposed relation relative to one another. Tissue-treating plates 114, 124 are formed from an electrically conductive material, e.g., for conducting electrical energy therebetween for treating tissue, although tissue-treating plates 114, 124 may alternatively be configured to conduct any suitable energy, e.g., thermal, microwave, light, ultrasonic, etc., through tissue grasped therebetween for energy-based tissue treatment. As mentioned above, tissue-treating plates 114, 124 are coupled to activation switch 4 and the source of energy (not shown), e.g., via the wires (not shown) extending from cable 2 through forceps 10, such that energy may be selectively supplied to tissue-treating plate 114 and/or tissue-treating plate 124 and conducted therebetween and through tissue disposed between jaw members 110, 120 to treat tissue.

One or both of jaw members 110, 120 may further define a longitudinally-extending channel 125 (only the channel 125 of jaw member 120 is shown) for allowing reciprocation of the cutting mechanism 85 upon actuation of trigger 62. Actuation of the trigger 62 reciprocates a knife drive rod, e.g., knife drive rod 280 of FIG. 2B, operably coupled to the cutting mechanism, e.g., knife 285. Together and as used herein, the knife, e.g., knife 285 and knife drive rod, e.g., knife drive rod 280, form a knife assembly 250. Knife drive rod 280 is made from a flexible material of sufficient strength to allow the knife drive rod 280 to both push and pull the knife 285 through tissue disposed between jaw members 110, 120. Moreover, the flexibility of the knife drive rod 280 allows the knife drive rod 280 to flex as needed during articulation of the jaw members 110, 120. The knife drive rod 280 may be made from a variety of flexible materials that exhibit the necessary strength and flexibility to allow smooth translation of the knife drive rod 280 through one or more articulating joints of articulating section 15 such as: NiTiNOL, stainless Steel or high carbon steel, Inconel, Monel, Nimonic, Nitronic, Hastelloy (Nickel based alloys other than NiTiNOL), Elgiloy (Cobalt-Nickel), Brass, Phosphor Bronze, Beryllium Copper, Chrome-Vanadium or Chrome-Silicon, Titanium, and/or Braided Cable (i.e. Steel or Tungsten).

The knife drive rod 280 generally refers to a drive member that may be in the shape of a rod, cable, braided cable, tube, piece of sheet metal or plastic, screw and the like. It is envisioned that the term "rod" covers all of these and other commonly known types of drive members made from a variety of different materials so long as it is strong enough, durable enough and/or stiff enough to advance and retract the knife 285.

Knife 285 is typically made from a stronger, harder, stiffer, and/or more durable material, e.g., stainless steel, to allow the knife 285 to easily translate through tissue on a repeated basis. Other materials are also contemplated such as: Stainless Steel or High Carbon Steel, Tool Steel, High Speed Steel, Chrome Steel, Tungsten Carbide, Titanium, Vanadium Alloys, Ceramic, Glass, and/or Plastic.

Since it is often difficult to assure a consistent and strong weld between two dissimilar metals, i.e., utilizing a flexible first material, e.g., Nitinol, for the knife drive rod 280 with a second stronger material for the knife 285, e.g., stainless steel, various welding, swaging and mechanical capture techniques are described below with respect to FIGS. 2A-10.

Figure 1C:
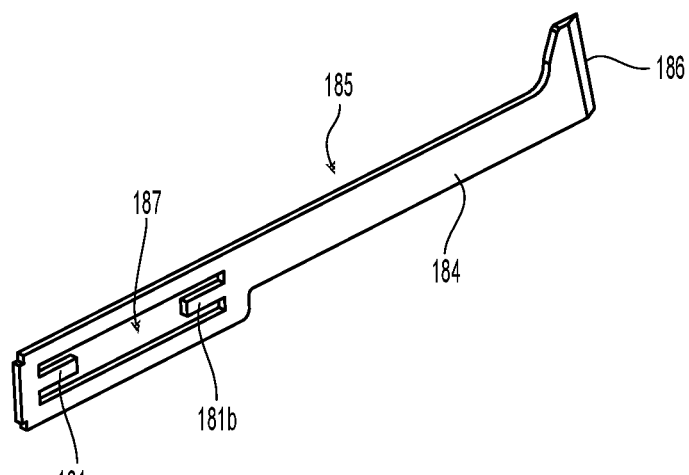
FIGS. 1C and 1D are enlarged schematic views of one embodiment of an engagement feature for coupling a knife blade to a knife drive rod exemplifying the aspects and features of the present disclosure.
Figure 1D:
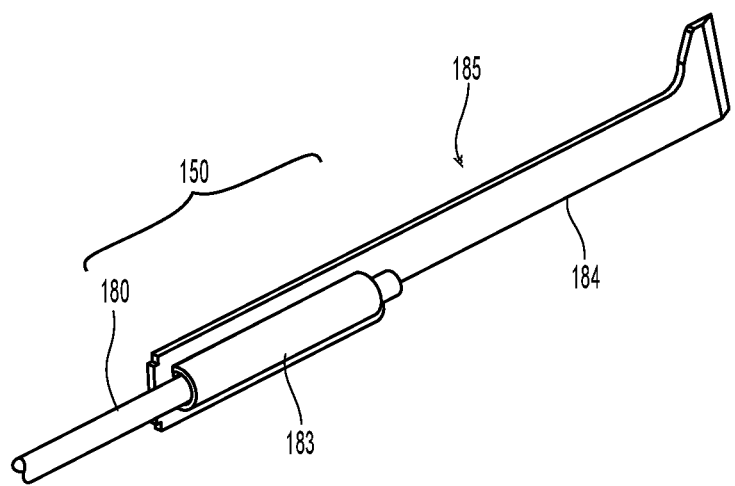

As mentioned above, because of the articulation of the shaft 12, a flexible wire or drive rod, e.g., drive rod 180 of FIG. 1D, needs to be used to push or pull a knife 185. To minimize the length of the shaft 12 and the so called "dead space" (the space between the end of the articulation section 15 and the jaw members 110, 120) the length of the knife 185 attached to the drive rod 180 should be minimized which will enhance usability and surgical access. The knife 185 still needs to retract proximally enough to clear the tissue stop (not shown) of the jaw members 110, 120 without retracting into any portion of the articulation section 15. This ensures proper articulation and allows the forceps 10 to deploy the knife 185 with minimal friction and wear. However, this typically requires that additional length needs to be added to the shaft 12 to house the retracted knife between the jaw members 110, 120 and the articulating section 15. FIGS. 1C-8B show various retention mechanisms and methods of attaching a shorter knife 185 to the knife drive rod 180.

FIGS. 1C and 1D show an embodiment of the knife 185 for engagement to the knife drive rod 180 that minimizes dead space between the articulating section 15 and the jaw members 110, 120. More particularly, knife 185 includes a knife body 184 having a distal end 186 and a proximal end 182, the distal end 186 including a sharpened edge for cutting tissue and the proximal end 182 including an aperture 187 defined therein for capturing the knife drive rod 180. Together the knife 185 and knife drive rod 180 form a knife assembly 150. A pair of opposing capture tabs 181a and 181b are etched (or otherwise formed) from the proximal end 182 into the aperture 187 and are configured to capture and secure a tube 183 therebetween. The inner periphery of the tube 183 is configured to engage, e.g., threadably engage, the knife drive rod 180. During assembly, the tube 183 and the knife drive rod 180 may be welded, e.g., spot-welded, laser welded, inductively welded, bead welded, etc. or crimped after engagement within the tube 183 to provide additional engagement of the knife drive rod 180 therein.

Since the knife drive rod 180 needs to be flexible to accommodate articulation of the jaw members 110, 120, and the knife body 184 needs to be sufficiently strong to cut through tissue on a repeated basis, the knife drive rod 180 and the knife body 184 are typically made from dissimilar materials and any such weld or bond may be weaker than desired. Thus, additional mechanical engagement between the two elements, e.g., the knife drive rod 180 and knife body 184, is needed to prevent mechanical failure. Tube 183 may be made from any type of metal, e.g., stainless steel, that will provide a secure weld to knife body 184. In embodiments, the knife body 184 and the tube 183 are made from the same material, e.g., stainless steel, to assure a good weld. The tube 183 may also be welded to the knife 185 along the top and/or bottom length of the tube 183.

By providing a strong mechanical connection between the knife drive rod 180 and the tube 183 and a strong mechanical connection between the tube 183 and the knife body 184, the chances of mechanical failure is greatly reduced.

FIGS. 1C and 1D show the knife 185 extended beyond the attachment point. Only a necessary portion of the distal end 184 of the knife 185 projects beyond the connection to the knife drive rod 180 to minimize dead space. For a curved jaw design, this would ensure the attachment tube 183 and drive rod 180 do not enter the curved portion of the jaw members, 110, 120.

Figure 2A:
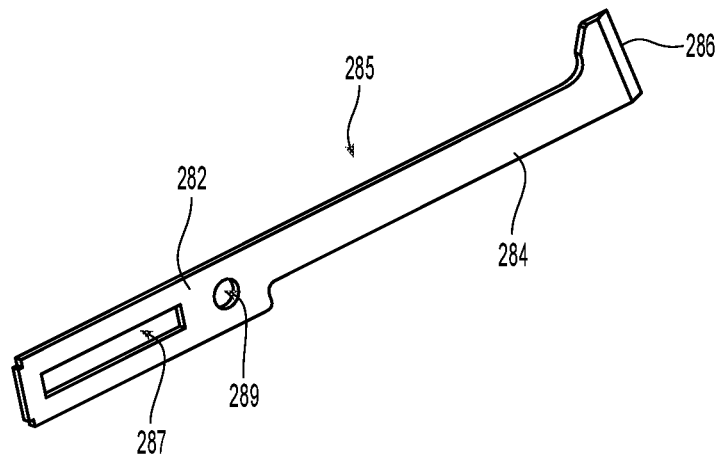
FIGS. 2A and 2B are enlarged schematic views of another embodiment of an engagement feature for coupling a knife blade to a knife drive rod exemplifying the aspects and features of the present disclosure.
Figure 2B:
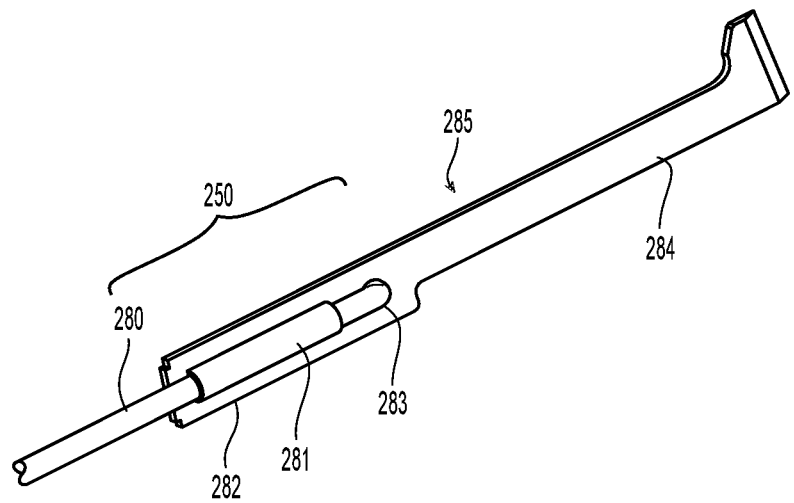

FIGS. 2A-2B show another embodiment of a knife 285 for engagement to a knife drive rod 280. More particularly, knife 285 includes a knife body 284 having a distal end 286 and a proximal end 282, the distal end 286 including a sharpened edge for cutting tissue and the proximal end 282 including a slot 287 defined therein and configured to capture a tube 281 crimped, threaded or welded onto a portion of the knife drive rod 280. Together the knife 285 and knife drive rod 280 form a knife assembly 250.

Since the knife drive rod 280 needs to be flexible to accommodate articulation of the jaw members 110, 120, and the knife body 284 needs to be sufficiently strong to cut through tissue on a repeated basis, the knife drive rod 280 and the knife body 284 are typically made from dissimilar materials and any such weld or bond may be weaker than desired. Thus additional mechanical engagement between the two elements, e.g., the knife drive rod 280 and knife body 284, is needed to prevent mechanical failure. Tube 281 may be made from any type of metal, e.g., stainless steel, that will provide a secure weld to knife body 284.

In embodiments, the knife body 284 and the tube 281 are made from the same material, e.g., stainless steel, to assure a good weld. The proximal end 282 of the knife body 280 also includes an aperture 289 defined therein configured to receive the distal end 283 of the knife drive rod 280. More particularly, the distal end 283 of the knife rod 280 is bent at an angle, e.g., 90°, such that during assembly the distal end 283 may be inserted into aperture 289 to secure the knife drive rod 280 to the knife body 284. In addition and during assembly the tube 281 is seated within slot 287 to capture the tube 281 therein and provide additional mechanical engagement between the knife drive rod 280 and the knife body 284. Only a necessary portion of the distal end 284 of the knife 285 projects beyond the connection to the knife drive rod 280 to minimize dead space.

Figure 3:
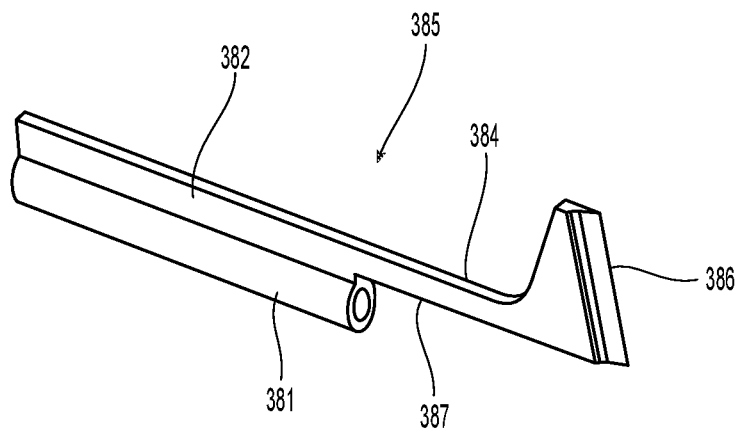
FIG. 3 is an enlarged schematic view of another embodiment of an engagement feature for coupling a knife blade to a knife drive rod exemplifying the aspects and features of the present disclosure.

FIG. 3 shows another embodiment of a knife 385 for engagement to a knife drive rod 380. More particularly, knife 385 includes a knife body 384 having a distal end 386 and a proximal end 382, the distal end 386 including a sharpened edge for cutting tissue and the proximal end 382 configured to mechanically engage a tube 381 which may be crimped, threaded or welded onto the proximal end 382 along a lower edge 387 of the knife body 384. Together the knife 385 and knife drive rod (not shown) form a knife assembly (not shown). Tube 381 may be made from any type of metal, e.g., stainless steel, that will provide a secure weld to knife body 384.

In embodiments, the knife body 384 and the tube 381 are made from the same material, e.g., stainless steel, to assure a good weld. The knife drive rod is secured within the tube 381 during assembly via crimping, welding, swaging or threadable engagement. Engaging the knife drive rod to the tube 381 which is secured to the lower edge 387 of the knife body 384 facilitates a more balanced actuation of the knife 385 during translation since the mechanical engagement of the knife body 384 and the tube 381 is along the centerline (lower edge 387) of the knife 385. Hereagain, only a necessary portion of the distal end 384 of the knife 385 projects beyond the connection to the knife drive rod to minimize dead space. In embodiments, the knife drive rod and/or the above described retention feature may provide a width or depth to the knife 385 that may be utilized to facilitate retention of the knife 385 within the jaw members 110, 120 or channel (not shown) defined within one or both jaw members 110, 120.

Figure 4:
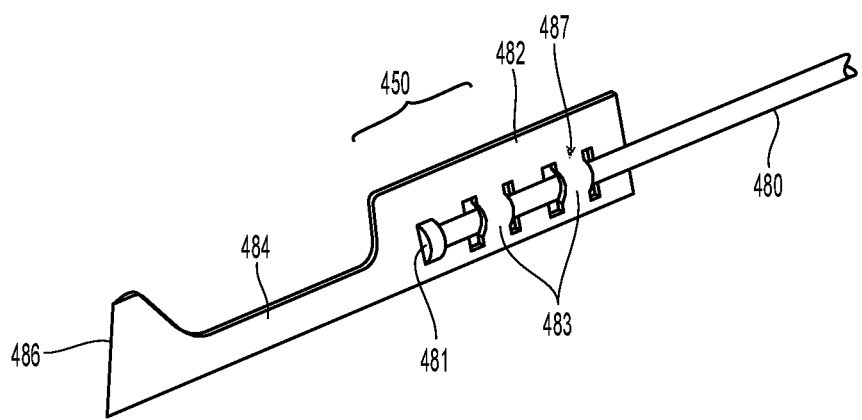
FIG. 4 is an enlarged schematic view of another embodiment of an engagement feature for coupling a knife blade to a knife drive rod exemplifying the aspects and features of the present disclosure.

FIG. 4 shows another embodiment of a knife 485 for engagement to a knife drive rod 480. More particularly, knife 485 includes a knife body 484 having a distal end 486 and a proximal end 482, the distal end 486 including a sharpened edge for cutting tissue and the proximal end 482 including an aperture 487 defined therein for capturing the knife drive rod 480. Together the knife 485 and knife drive rod 480 form a knife assembly 450. A series of fins 483 are etched from the proximal end 482 into the aperture 487 that include one or more recessed portions (not shown) defined therein configured to partially receive the outer periphery of the knife drive rod 480 to mechanically capture the knife drive rod 480 on opposing sides along the length thereof. During assembly, the knife drive rod 480 is weaved through the various fins 483 to engage the recesses and secure the knife drive rod 480 to the knife 485. Weaving the knife drive rod 480 through the fins 483 provides lateral stability to the knife 485 and knife drive rod 480 during use. Once the knife drive rod 480 is weaved through the fins 483, a retention mechanism, e.g., a cap 481, is secured (e.g., welded, swaged, crimped, etc.) to the end of the knife drive rod 480 to lock the knife drive rod 480 in place within aperture 487 of knife 485. It is envisioned that any other type of enlarged area at the distal end can function as a retention mechanism, e.g., forged end, bubble-like end, additional pieces welded, crimped or swaged to end, etc. The dimensions of the cap 481 are sized greater than the dimensions of the recesses to prevent slippage of the mechanical connection during use. The knife 485 may be made from stainless steel, e.g., surgical stainless steel (316 SS) or other surgical metal, and the knife drive rod 480 may be made from Nitinol or other flexible metal or a metal hybrid (Nitinol inner rod and helical hollow strand HHS outer casing). Again, only a necessary portion of the distal end 484 of the knife 485 projects beyond the connection to the knife drive rod 480 to minimize dead space.

Figure 5A:
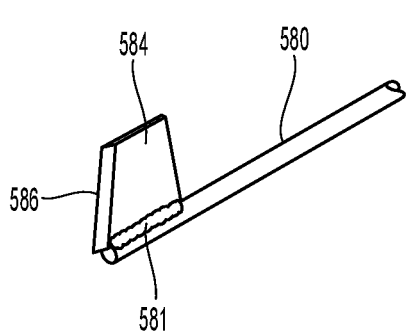
FIGS. 5A and 5B are enlarged schematic views of another embodiment of an engagement feature for coupling a knife blade chip to a knife drive rod exemplifying the aspects and features of the present disclosure.
Figure 5B:
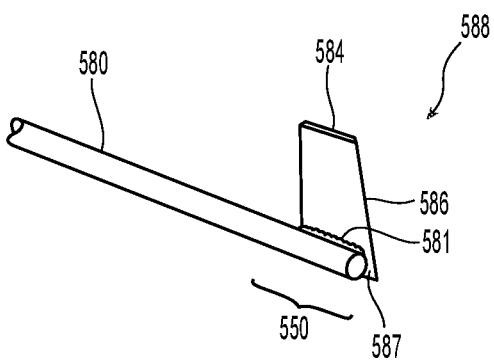

FIGS. 5A and 5B show another embodiment of a knife 585 for engagement to a knife drive rod 580. More particularly, knife 585 includes a knife body 584 having a distal end 586 and a proximal end 582, the distal end 586 including a sharpened edge for cutting tissue and the proximal end 582 including lower edge 587 including an inner facing surface configured to engage the knife drive rod 580 via welding, or swaging along a weld 581. Together the knife 585 and knife drive rod 580 form a knife assembly 550. Knife 585 is generally chip-like as compared to the other knives, e.g., knife 285, described herein and, in this particular embodiment, the knife 585 is welded directly to the knife drive rod 580.

Since the knife drive rod 580 needs to be flexible to accommodate articulation of the jaw members 110, 120, and the knife body 584 needs to be sufficiently strong to cut through tissue on a repeated basis, the knife drive rod 580 and the knife body 584 are typically made from dissimilar materials and any such weld or bond may be weaker than desired. Thus additional mechanical engagement between the two elements, e.g., the knife drive rod 580 and knife body 584, may be needed to prevent mechanical failure. Any one of the aforementioned additional retention features may be implemented with chip-like knife 585 to produce a stronger engagement. On the other hand, the knife 585 and the knife drive rod 580 may be made from the same type of material, e.g., stainless steel, that will provide a secure weld to knife body 584.

In addition and during assembly the knife drive rod 580 may be seated within a recess (not shown) defined in a side of the knife 585 to at least partially capture the knife drive rod 580 therein and provide additional mechanical engagement between the knife drive rod 580 and the knife body 584.

Figure 6:
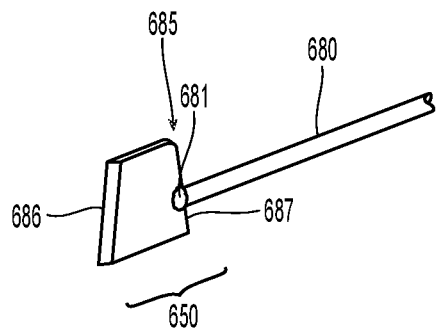
FIG. 6 is an enlarged schematic views of another embodiment of an engagement feature for coupling a knife blade chip to a knife drive rod exemplifying the aspects and features of the present disclosure.

FIG. 6 shows another embodiment of a knife 685 for engagement to a knife drive rod 680. More particularly, knife 685 includes a knife body 684 having a distal end 686 and a proximal end 682, the distal end 686 including a sharpened edge for cutting tissue and the proximal end 682 including a rear edge 687 including an inner facing surface configured to engage the knife drive rod 680 via welding or swaging. Together the knife 685 and knife drive rod 680 form a knife assembly 650. Knife 685 is generally chip-like similar to the embodiment shown in FIGS. 5A and 5B, and, in this particular embodiment, the proximal or rear edge of knife 685 is welded directly to the knife drive rod 680. In addition and during assembly the knife drive rod 680 may be seated within a recess (not shown) defined in the proximal or rear edge of the knife 685 to at least partially capture the knife drive rod 680 therein and provide additional mechanical engagement between the knife drive rod 680 and the knife body 684.

Moreover, any one of the aforementioned additional retention features may be implemented with chip-like knife 685 to produce a stronger engagement. On the other hand, the knife 685 and the knife drive rod 680 may be made from the same type of material, e.g., stainless steel, that will provide a secure weld to knife body 684.

Figure 7:
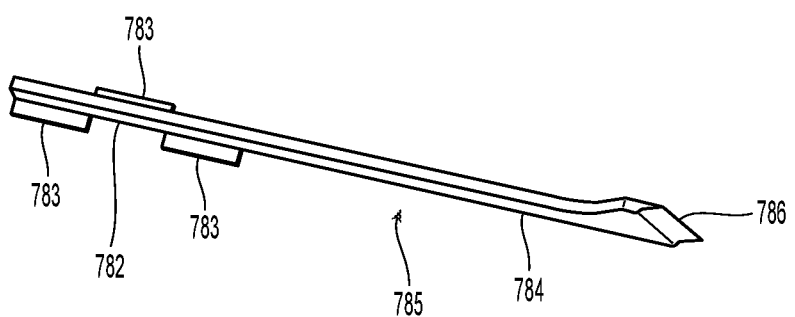
FIG. 7 is an enlarged schematic view of another embodiment of an engagement feature for coupling a knife blade to a knife drive rod exemplifying the aspects and features of the present disclosure.

FIG. 7 shows another embodiment of a knife 785 for engagement to a knife drive rod (not shown). More particularly, knife 785 includes a knife body 784 having a distal end 786 and a proximal end 782, the distal end 786 including a sharpened edge for cutting tissue and the proximal end 782 including a series of retention tabs 783 that project generally laterally therefrom. The retention tabs may be stamped or etched in the proximal end 782 and are configured to capture and secure the knife drive rod. During assembly, the knife drive rod and the retention tabs 783 may be welded, e.g., spot-welded, laser welded, or crimped after engagement to provide additional engagement of the knife drive rod to the knife 785.

Since the knife drive rod needs to be flexible to accommodate articulation of the jaw members 110, 120, and the knife body 784 needs to be sufficiently strong to cut through tissue on a repeated basis, the knife drive rod and the knife body 784 are typically made from dissimilar materials and any such weld or bond may be weaker than desired. Thus additional mechanical engagement between the two elements, e.g., the knife drive rod and knife body 784, may be needed to prevent mechanical failure. Retention tabs 783 may be made from any type of metal that will provide a secure weld to knife drive rod. In embodiments, the knife body 784 and the knife drive rod are made from the same material, e.g., stainless steel, to assure a good weld. By providing a strong mechanical connection between the knife drive rod and the retention tabs 783, the chances of mechanical failure is greatly reduced.

Alternatively, the retention tabs 783 may be utilized to retain the knife 785 within a knife channel (not shown) defined within one or both jaw members 110, 120. In this instance, the knife 785 would be attached or otherwise engaged to the knife drive rod 780 by way of one or more of the retention features or retention methods described herein. In embodiments, the knife drive rod 780 and/or any of the above described retention features may provide a width to the knife 785 that may be utilized to facilitate retention of the knife 785 within the jaw members 110, 120 or channel (not shown) defined within one or both jaw members 110, 120.

Figure 8A:
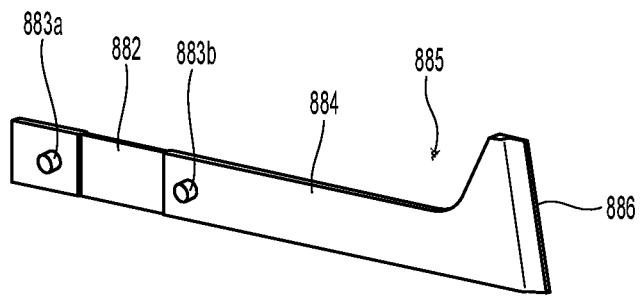
FIGS. 8A and 8B are enlarged schematic views of another embodiment of an engagement feature for coupling a knife blade to a knife drive rod exemplifying the aspects and features of the present disclosure.
Figure 8B:
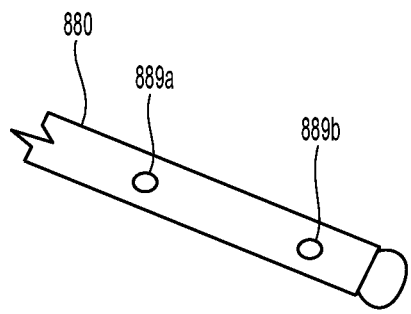

FIGS. 8A and 8B show another embodiment of a knife 885 for engagement to a knife drive rod 880. More particularly, knife 885 includes a knife body 884 having a distal end 886 and a proximal end 882, the distal end 886 including a sharpened edge for cutting tissue and the proximal end 882 including one or more detents 883a, 883b projecting therefrom configured to capture the knife drive rod 880. More particularly, the knife drive rod 880 includes a corresponding one or more apertures 889a, 889b defined therein and configured to operably engage the detents 883a, 883b upon assembly. Once engaged, the knife drive rod 880 may be welded, riveted, or swaged to the knife 885. Alternatively or in addition to, the detents 883a, 883b may be spot-welded within the apertures 889a, 889b to further secure the knife drive rod 880 to the knife 885.

The detents 883a, 883b of the knife 885 and the knife drive rod 880 may be made from any type of metal that will provide a secure weld. Since a majority of the extension and retraction forces associated with translating the knife 885 will be offloaded by the mechanical engagement of the detents 883a, 883b and apertures 889a, 889b, the additional weld would not necessarily need to be strong (unlike some of the aforedescribed embodiments). As such, the knife 885 and the knife drive rod 880 do not necessarily need to be made from the same type of material to insure a secure weld. Thus, a flexible super elastic material, e.g., Nitinol, may be used for the knife drive rod 880 and stainless steel may be utilized for the knife 885.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing including at least one actuator disposed thereon;
an elongated shaft extending from a distal portion of the housing, the elongated shaft including an end effector assembly engaged at a distal end thereof, the end effector assembly including a pair of opposing jaw members, at least one of the jaw members including a knife channel defined therein;
an articulation section disposed between the housing and the end effector assembly, the articulation section configured to selectively articulate the end effector assembly upon actuation of the at least one actuator, the articulation section and a proximal end of the knife channel defining a first distance therebetween; and
a knife assembly including:
a knife having proximal and distal ends defining a knife length therebetween, the proximal end including an engagement feature disposed thereon; and
a knife drive rod configured to operably engage the engagement feature to secure the knife drive rod to the knife such that the distal end of the knife extends beyond the engagement feature and wherein the knife length is less than the length of the first distance, wherein the knife drive rod is configured to advance the knife through the knife channel, and the engagement feature includes an aperture defined within the knife, the aperture configured to receive a bent end of the knife drive rod.

2. The surgical instrument according to claim 1, wherein the engagement feature includes a slot defined within a proximal end of the knife and configured to support a portion of the knife drive rod proximate the bent end thereof.

3. The surgical instrument according to claim 1, wherein the engagement feature includes a slot defined within a proximal end of the knife and configured to capture a tube therein disposed about the knife drive rod proximate the bent end thereof.

4. The surgical instrument according to claim 3, wherein the tube is at least one of crimped, threaded or welded onto the portion of the knife drive rod proximate the bent end.

5. The surgical instrument according to claim 3, wherein the tube and the knife are welded to mechanically secure the tube within the slot.

6. The surgical instrument according to claim 3, wherein the tube and the knife are made from similar materials to insure a good weld within the slot.

7. The surgical instrument according to claim 6, wherein the knife drive rod is made from a dissimilar metal from the tube and the knife.

8. The surgical instrument according to claim 7, wherein the knife drive rod is made from a high strength, flexible material.

9. The surgical instrument according to claim 1, wherein the bent end of the knife drive rod includes an angle of about 90°.

10. A surgical instrument, comprising:
a housing;
an elongated shaft extending from a distal portion of the housing, the elongated shaft including an end effector assembly engaged at a distal end thereof, the end effector assembly including a pair of opposing jaw members, at least one of the jaw members including a knife channel defined therein;
an articulation section disposed between the housing and the end effector assembly, the articulation section being configured to selectively articulate the end effector assembly; and
a knife assembly including:
a knife having proximal and distal end portions, the proximal end portion including an engagement feature; and
a knife drive rod configured to be coupled to the engagement feature to secure the knife drive rod to the knife such that the distal end of the knife extends beyond the engagement feature, wherein the engagement feature includes:
an aperture defined within the knife, the aperture being configured to receive a bent end of the knife drive rod; and
a slot configured to capture a tube disposed about the knife drive rod.

11. The surgical instrument according to claim 10, wherein the tube is at least one of crimped, threaded or welded onto the portion of the knife drive rod proximate the bent end.

12. The surgical instrument according to claim 10, wherein the tube and the knife are welded to mechanically secure the tube within the slot.

13. The surgical instrument according to claim 10, wherein the tube and the knife are made from similar materials to insure a good weld within the slot.

14. The surgical instrument according to claim 13, wherein the knife drive rod is made from a dissimilar metal from the tube and the knife.

15. The surgical instrument according to claim 14, wherein the knife drive rod is made from a high strength, flexible material.

16. The surgical instrument according to claim 10, wherein the bent end of the knife drive rod includes an angle of about 90°.

17. The surgical instrument according to claim 10, wherein the slot of the engagement feature is defined within a proximal end of the knife and is configured to support a portion of the knife drive rod proximate the bent end.

* * * * *